United States Patent
Wang et al.

(10) Patent No.: US 12,214,329 B2
(45) Date of Patent: Feb. 4, 2025

(54) NICOTINAMIDE DUMMY TEMPLATE SURFACE MOLECULARLY IMPRINTED POLYMER AND PREPARATION METHOD AND APPLICATION THEREOF

(71) Applicant: Jiangnan University, Wuxi (CN)

(72) Inventors: Hongxin Wang, Wuxi (CN); Jingyu Chen, Wuxi (CN); Shijia Wu, Wuxi (CN); Xinlin Wei, Wuxi (CN); Xin Huang, Wuxi (CN); Li Wang, Wuxi (CN)

(73) Assignee: Jiangnan University, Wuxi (CN)

( * ) Notice: Subject to any disclaimer, the term of this patent is extended or adjusted under 35 U.S.C. 154(b) by 634 days.

(21) Appl. No.: 17/551,338

(22) Filed: Dec. 15, 2021

(65) Prior Publication Data

US 2022/0105491 A1 Apr. 7, 2022

Related U.S. Application Data

(63) Continuation of application No. PCT/CN2020/105396, filed on Jul. 29, 2020.

(30) Foreign Application Priority Data

Nov. 28, 2019 (CN) .......................... 201911188009.9

(51) Int. Cl.
*B01J 20/26* (2006.01)
*A23F 3/20* (2006.01)
(Continued)

(52) U.S. Cl.
CPC ............. *B01J 20/268* (2013.01); *A23F 3/205* (2013.01); *B01D 15/22* (2013.01);
(Continued)

(58) Field of Classification Search
CPC ...... B01J 20/268; B01J 20/3085; A23F 3/205; C08F 292/00; C07C 37/82; C07C 231/24
See application file for complete search history.

(56) References Cited

FOREIGN PATENT DOCUMENTS

| CN | 103478337 A | 1/2014 | |
|---|---|---|---|
| CN | 104892868 A * | 9/2015 | ............... B01D 1/08 |

(Continued)

OTHER PUBLICATIONS

CN106674405(A), Zheng Xiaoman et al., Molecularly imprinted polymeric microspheres as well as preparation method and application thereof, 10 pages, English translation (Year: 2017).*

(Continued)

*Primary Examiner* — Yate' K Cutliff
(74) *Attorney, Agent, or Firm* — IPRO, PLLC; Na Xu

(57) ABSTRACT

The disclosure discloses a nicotinamide dummy template surface molecularly imprinted polymer, a preparation method and application thereof, and belongs to the technical field of chemical materials. The preparation method of the disclosure includes the steps of preparing a modified silica gel carrier, preparing a dummy template surface molecularly imprinted polymer and the like. The disclosure uses nicotinamide, a structural analogue of imidacloprid and acetamiprid, as a dummy template to prepare a silica gel surface molecularly imprinted polymer. The polymer not only can effectively avoid pollution caused by the leakage of template molecules, but also can specifically remove imidacloprid and acetamiprid from water-soluble tea extracts. The removal rate of imidacloprid and acetamiprid is greater than 96% and 93%, respectively, and the loss of tea polyphenols in the extracts is less than 10%. In addition, the molecularly imprinted adsorption column prepared by the disclosure can be eluted with ethanol solution, and the eluted adsorption column can be recycled, so the disclosure can be well (Continued)

applied to the preparation technology of tea extracts and has good application prospects.

6 Claims, 5 Drawing Sheets

(51) Int. Cl.
    *B01D 15/22*     (2006.01)
    *B01J 20/30*     (2006.01)
    *C07C 37/82*     (2006.01)
    *C07C 231/24*     (2006.01)
    *C08F 292/00*     (2006.01)

(52) U.S. Cl.
    CPC ........... *B01J 20/3085* (2013.01); *C07C 37/82* (2013.01); *C07C 231/24* (2013.01); *C08F 292/00* (2013.01); *B01J 2220/46* (2013.01); *B01J 2220/4806* (2013.01); *B01J 2220/4812* (2013.01)

(56) References Cited

FOREIGN PATENT DOCUMENTS

| CN | 106674405 A | * | 5/2017 | ............. B01J 13/04 |
| CN | 110511423 A | | 11/2019 | |
| CN | 110951105 A | | 4/2020 | |
| WO | 2013190506 A1 | | 12/2013 | |

OTHER PUBLICATIONS

CN104892868 (A), Chen Fangyan et al., Silica gel surface molecularly imprinted polymer with specific adsorption of DEHP and preparation method and application theeof, 16 pages, English translaiton (Year: 2015).*

Li Minting et. al., "Molecularly imprinted polymers on a silica surface for the adsorption of tobacco-specific nitrosamines in mainstream cigarette smoke", J.Sep.Sci., V38, Issue 14,Dec. 31, 2015, pp. 2551-2557.

Liang, Xiao-yun et al., "Preparation of imidacloprid-imprinted polymer and its application as a solid phase extract", Chinese J. of Analysis Laboratory, V27, No. 5, May 2008, pp. 9-12.

* cited by examiner

NICOTINAMIDE DUMMY TEMPLATE SURFACE MOLECULARLY IMPRINTED POLYMER AND PREPARATION METHOD AND APPLICATION THEREOF

TECHNICAL FIELD

The disclosure herein relates to a nicotinamide dummy template surface molecularly imprinted polymer and a preparation method and application thereof, and belongs to the technical field of chemical materials.

BACKGROUND

Water-soluble tea extracts, especially tea polyphenols, are polyhydroxy phenolic compounds. As the main chemical components with health-care functions in tea, tea polyphenols are the main products of deep processing of tea. One of the main problems faced in the processing of tea polyphenols is pesticide residues. Pesticide residues in tea polyphenols will not only affect the quality of tea and harm the health of consumers, but also damage the brand reputation of manufacturers. Imidacloprid and acetamiprid, commonly used high-efficiency chloronicotinoid insecticides in tea planting, have good solubility in water and organic solvents, thus they are very easy to remain in the processing of tea polyphenols. At present, the removal methods of pesticide residues mainly include physical methods, chemical methods (KUSVURAN E, YILDIRIM D, MAVRUK F, et al. Removal of chloropyrifos ethyl, tetradifon and chlorothalonil pesticide residues from citrus by using ozone[J]. Journal of Hazardous Materials, 2012, 241(4):287-300. AFFAM A C, CHAUDHURI M. Degradation of pesticides chlorpyrifos, cypermethrin and chlorothalonil in aqueous solution by TiO2 photocatalysis[J]. 2013, 130(1):160-165.) and biological methods (FERRARIO C, PITTINO F, TAGLIA-FERRI I, et al. Bacteria contribute to pesticide degradation in cryoconite holes in an Alpine glacier[J]. Environmental Pollution, 2017, 230:919-926.). Among them, the chemical and biological methods are not suitable for the removal of pesticides from tea polyphenols due to safety issues. In the physical adsorption methods, activated carbon (MARCZEWSKI A W, SECZKOWSKA M, DERYŁO-MARCZEWSKA A, et al. Adsorption equilibrium and kinetics of selected phenoxyacid pesticides on activated carbon: effect of temperature[J]. Adsorption-journal of the International Adsorption Society, 2016, 22(4-6):1-14.), zeolite (HUONG P. Nitrophenols removal from aqueous medium using Fe-nano mesoporous zeolite [J]. Materials & Design, 2016, 101:210-217.) and some polymer materials (ZOLFAGHARI G. β-Cyclodextrin incorporated nanoporous carbon: Host-guest inclusion for removal of p-Nitrophenol and pesticides from aqueous solutions[J]. Chemical Engineering Journal, 2016, 283:1424-1434.) have been developed for the removal of pesticide residues. However, in order to reduce the loss of tea polyphenols in the process of pesticide removal and ensure the quality and purity of final products, it is necessary to choose a material with high selectivity to imidacloprid and acetamiprid.

Molecular imprinting technology (MIT) is an emerging technology with specific recognition functions developed by combining polymer chemistry, biochemistry and other disciplines. A functional recognition material artificially synthesized by MIT, which has the characteristics of high stability, high selectivity and easy preparation, is called molecularly imprinted polymer (MIP). So far, MIP has been used to remove hazardous substances in many studies. For example, Sánchez-Polo (SÁNCHEZ-POLO M, VELO-GALA I, LÓPEZ-PEÑALVER J J, et al. Molecular imprinted polymer to remove tetracycline from aqueous solutions[J]. Microporous and Mesoporous Materials, 2015, 203(203):32-40.) successfully synthesized a molecularly imprinted polymer capable of removing tetracycline (TC) from water. Similarly, a molecular imprinted solid phase extraction material for the adsorption of Th(IV) has also been studied (JI X Z, LIU H J, WANG L L, et al. Study on adsorption of Th(IV) using surface modified dibenzoylmethane molecular imprinted polymer[J]. Journal of Radioanalytical & Nuclear Chemistry, 2013, 295(1):265-70.). However, there is no study on simultaneous adsorption of imidacloprid and acetamiprid with MIP at present. Dummy template molecular imprinting is a technology that can effectively avoid template leakage. In actual sample applications, template leakage will cause serious pollution in separation process. Nicotinamide is a structural analog of imidacloprid and acetamidine, and has lower toxicity than imidacloprid and acetamidine. Niacinamide, which is often used as food additives, cosmetics and medicines for its anti-inflammatory effects, is widely considered to be safer. Choosing nicotinamide as a dummy template can not only remove imidacloprid and acetamiprid simultaneously and avoid pesticide pollution caused by template leakage, but also be more acceptable to consumers.

SUMMARY

To solve the problem of pesticide residues in the tea extract aqueous solution, the disclosure uses nicotinamide, a structural analogue of imidacloprid and acetamiprid, as a dummy template molecule. Not only a surface molecularly imprinted polymer that can simultaneously remove imidacloprid and acetamiprid can be prepared, but also the pollution caused by the leakage of template molecules can be effectively avoided so that the safety of the material can be improved. A solid phase extraction adsorption column prepared by using the polymer as the column packing can effectively remove imidacloprid and acetamiprid from the tea extract aqueous solution while the loss of tea polyphenols is small, so the polymer has broad application prospects in green processing of water-soluble tea extracts. In view of this, the disclosure provides a nicotinamide dummy template surface molecularly imprinted polymer and a preparation method and application thereof.

The first objective of the disclosure is to provide a preparation method of a nicotinamide dummy template surface molecularly imprinted polymer. The method includes the following steps:

S1. preparation of a modified silica gel carrier soaking granular silica gel in hydrochloric acid for treatment, filtering and washing the silica gel to neutral and drying the silica gel; mixing the dried silica gel with toluene at m/v (g/mL)=1:40-1:8; adding 3-aminopropyltriethoxysilane (APTS) and pyridine dropwise at a reaction temperature of 363-383 K in a nitrogen atmosphere, performing refluxing for 20-30 h; after washing the obtained mixture with toluene, acetone, ether and methanol, performing vacuum drying to obtain amino-modified silica gel;

mixing the amino-modified silica gel with toluene at m/v (g/mL)=1:40-1:8; adding acryloyl chloride in a nitrogen atmosphere, adding triethylamine dropwise after magnetic stirring, and performing stirring at room temperature for reacting for 20-30 h; after washing the obtained mixture with toluene, acetone, ether and methanol, performing vacuum drying to prepare acyl-modified silica gel;

S2. preparation of a dummy template surface molecularly imprinted polymer dissolving nicotinamide in a methanol aqueous solution at m/v (mg/mL)=1:1-3:1; adding the acyl-modified silica gel and methacrylic acid (MAA), and after ultrasonic dispersion, reacting for 2-6 h in the dark, where the mass ratio of the nicotinamide to the acyl-modified silica gel is 5:6-5:3; after the reaction, adding ethylene glycol dimethacrylate (EGDMA) and azobisisobuty-ronitrile (AIBN) in a nitrogen atmosphere, and performing sealed reaction at 323-343 K in a water bath for 20-28 h; removing the template by Soxhlet extraction, and performing washing and drying to prepare the dummy template surface molecularly imprinted polymer.

Preferably, in S1, the volume of the APTS added is 1/20-1/2 of toluene, and the volume of pyridine added is 1/80-1/8 of toluene.

Preferably, the volume of the acryloyl chloride added in S1 is 1/16-1/2 of toluene.

The second objective of the disclosure is a nicotinamide dummy template surface molecularly imprinted polymer prepared by the preparation method of the disclosure.

The third objective of the disclosure is the application of the nicotinamide dummy template surface molecularly imprinted polymer in removal of imidacloprid and acetamiprid from the tea extract aqueous solution.

Preferably, the steps of removing imidacloprid and acetamiprid from the tea extract aqueous solution with the nicotinamide dummy template surface molecularly imprinted polymer are as follows:

S1. preparation of a molecularly imprinted solid phase adsorption column wetly packing nicotinamide dummy template surface molecularly imprinting polymer (DMIP) into an SPE small column packed with a lower sieve plate and pressing into an upper sieve plate to obtain a molecular imprinted solid phase adsorption column; adding methanol to activate the column for later use;

S2. removal application adding imidacloprid and acetamiprid to a tea extract aqueous solution with a concentration of 10-60 wt % so the concentrations of imidacloprid and acetamiprid are 1-20 μg/mL respectively; using the aqueous solution as a loading solution and using the solid phase adsorption column prepared in S1 for adsorption; controlling the flow rate of the loading solution; washing off weakly retained compounds with 2-8 column volumes of deionized water; mixing the eluent and the column fluid and detecting the mixed solution;

S3. recycling eluting the adsorption column with the imidacloprid and acetamiprid in S2 with a mixed solvent of methanol-acetic acid in a volume ratio of 9:1, and adjusting and controlling the flow rate to 0.5-2 mL/min to recycle the adsorption column.

Preferably, the loss of water-soluble tea extracts in S2 is less than 10%, and the removal rate of imidacloprid and acetamiprid is greater than 96% and 93%, respectively.

Preferably, 96% or more of imidacloprid and 98% or more of acetamiprid in the adsorption column in S3 are eluted.

Preferably, the tea extracts are tea polyphenols or theanine.

Preferably, the weight percentage of the water-soluble tea extracts is 20-50 wt %.

Beneficial Effects:

The method of the disclosure novelly uses nicotinamide as a dummy template molecule to prepare a silica gel surface molecularly imprinted polymer. The polymer can specifically adsorb imidacloprid and acetamiprid from tea extracts, and the loss of tea polyphenols in tea extracts is small. The removal rate of imidacloprid and acetamiprid is greater than 96% and 93%, respectively, and the loss of tea polyphenols in the extracts is less than 10%. In addition, the adsorption column prepared by the disclosure can be recycled after being eluted with methanol/acetic acid solution, so the disclosure can be well applied to the processing technology of tea extracts and has good application prospects.

DETAILED DESCRIPTION

The exemplary examples of the disclosure will be described below. It should be understood that the examples are for better explaining the disclosure and are not intended to limit the disclosure.

Testing Method:

Accurately weigh 10 mg of the prepared DMIP and DNIP and place the DMIP and DNIP in 25 mL Erlenmeyer flasks respectively, and then add 8 mL of 0.2 mg/mL imidacloprid and acetamiprid aqueous solutions respectively. After shaking for 20 h at room temperature, perform centrifugation to collect the supernatant and dilute the supernatant to 4 mL with deionized water. Determine the concentrations of imidacloprid and acetamiprid in the supernatant by HPLC-MS-MS, and calculate the adsorption capacity Q (mg/g) and specific factor α. The calculation method is as shown in equation (1) and equation (2).

$$Q = \frac{(C_0 - C_t)V}{W} \quad (1)$$

$$\alpha = \frac{Q_m}{Q_n} \quad (2)$$

In equation (1), $C_0$ is initial concentration in mg/mL; $C_t$ is equilibrium concentration in mg/mL; V is solution volume in mL; and W is material mass in mg.

In equation (2), $Q_m$ is the adsorption capacity of DMIP in mg/g; and $Q_n$ is the adsorption capacity of DNIP in mg/g.

Example 1

Figure 1:
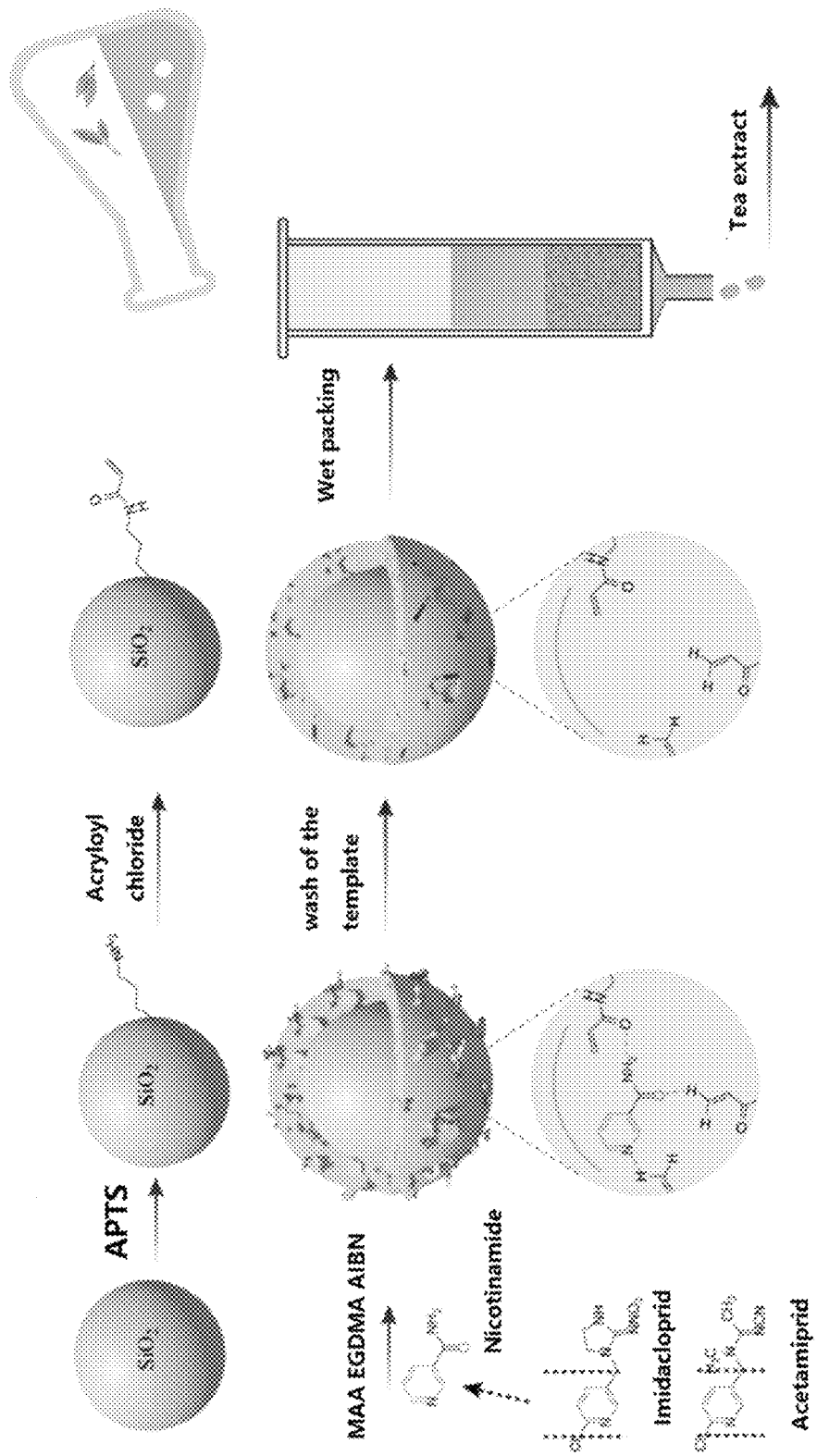
FIG. 1 is a technical flow chart of the method of the present disclosure.
Figure 2A:
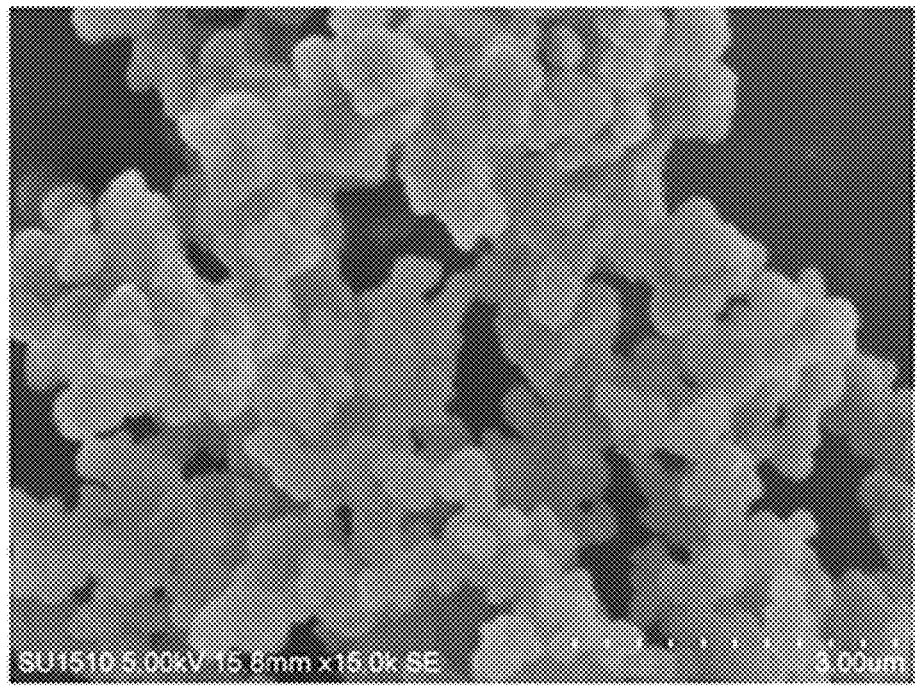
FIG. 2A is a scanning electron micrograph of the DMIP magnified 15000 times of Example 1.
Figure 2B:
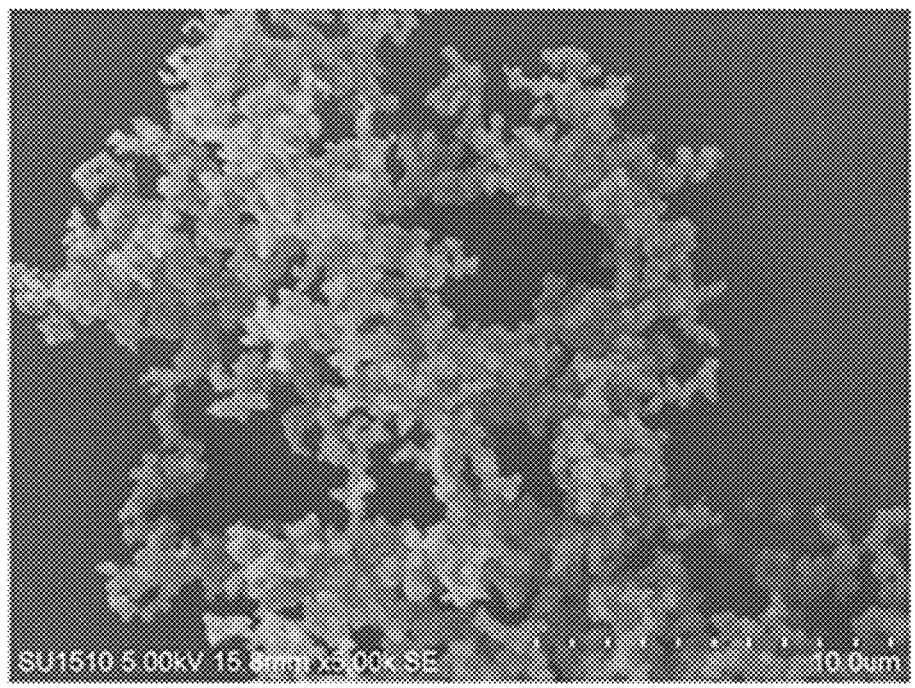
FIG. 2B is a scanning electron micrograph of the DMIP magnified 5000 times of Example 1.
Figure 2C:
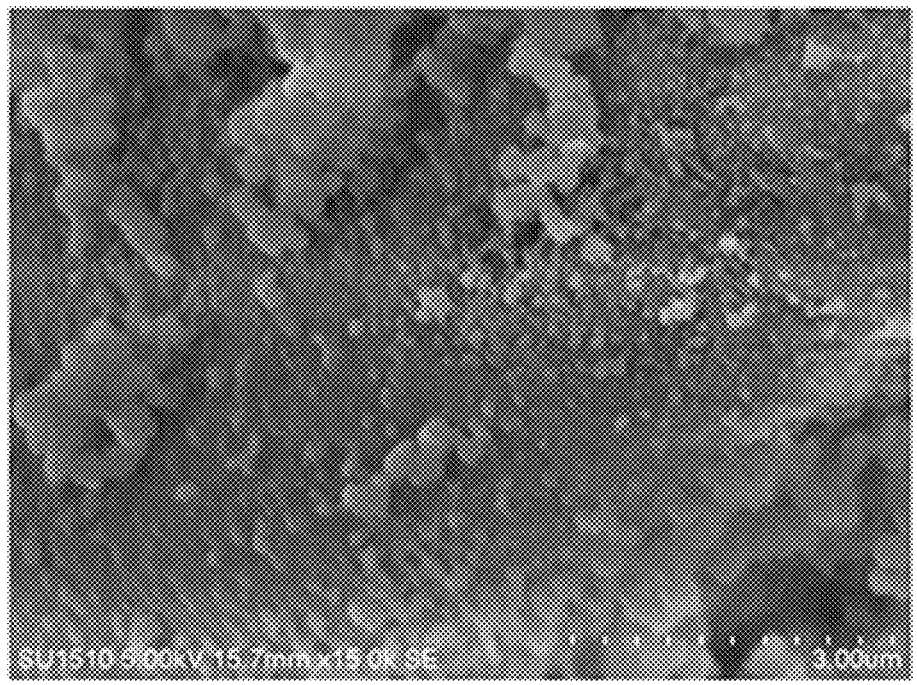
FIG. 2C is a scanning electron micrograph of the DNIP magnified 15000 times of Comparative Example 1.
Figure 2D:
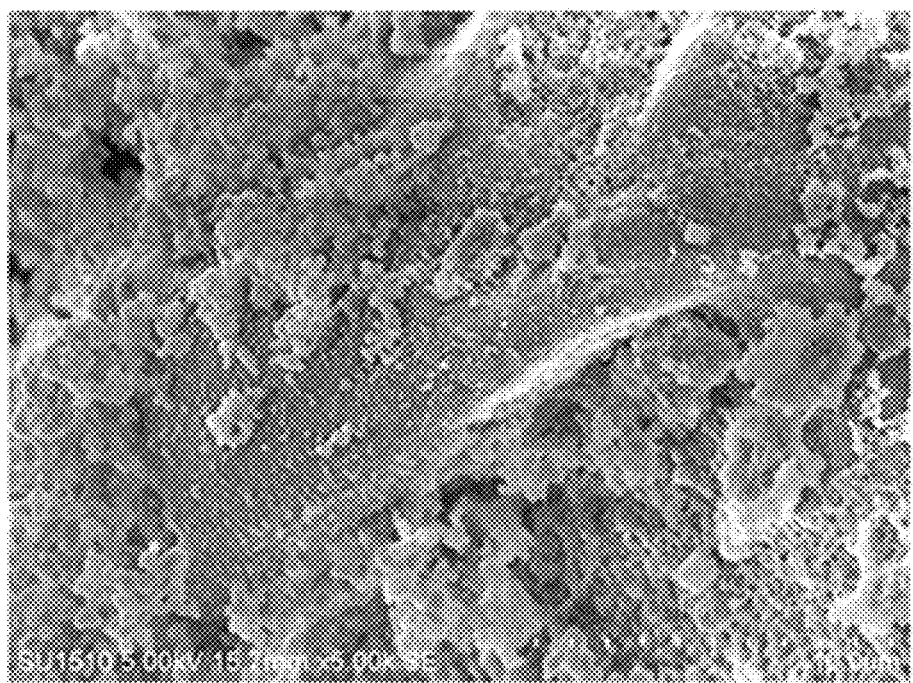
FIG. 2D is a scanning electron micrograph of the DNIP magnified 5000 times of Comparative Example 1.

The preparation method of the nicotinamide dummy template surface molecularly imprinted polymer is as shown in FIG. 1, and the method includes the following steps:

S1. Preparation of a modified a silica gel carrier 4 g of granular silica gel was soaked in 100 mL of 10 mol/L HCl solution and stirred for 24 h. After being filtered, the silica gel was washed with deionized water to neutral and dried. The dried silica gel was mixed with 50 mL of toluene, and 6 mL of APTS and an appropriate amount of pyridine were added dropwise and stirred under the protection of nitrogen for 20 min. The reaction system was controlled at 373 K and refluxed for 24 h. Then the obtained mixture was washed with toluene, acetone, ether and methanol, and finally dried in a vacuum oven for 8 h to prepare amino-modified silica gel.

4 g of amino-modified silica gel was mixed with 50 mL of toluene. 8 mL of acryloyl chloride was added under the protection of nitrogen and stirred magnetically for 10 min. An appropriate amount of triethylamine was added dropwise, and then stirred at room temperature for 24 h. The obtained compound was filtered and washed with toluene, acetone, ether and methanol, and then dried in a vacuum oven for 8 h to prepare acyl-modified silica gel.

S2. Preparation of a dummy template surface molecularly imprinted polymer 123.4 mg (about 1 mmoL) of nicotinamide was weighed and placed in a 250 mL round-bottomed flask, mixed and dissolved with 80 mL of methanol-water (the volume ratio of methanol to water is 90:10). Then 0.9 g of acyl-modified silica gel and 0.34 mL of MAA (4 mmol) were added and sonicated for 30 min. After fully dissolving and dispersing, the mixture was placed in the dark for 4 h to make template molecules and the functional monomer MAA fully interact. A cross-linking agent EGDMA (the molar ratio of the cross-linking agent EGDMA to the functional monomer MAA is 7:1) and AIBN (40 mg) were added to the mixture, and high-purity nitrogen was aerated for 20 min to maintain an inert atmosphere in the flask. The flask was sealed under the protection of nitrogen, and polymerization was thermally initiated in a 333 K water bath for 24 h. Using V (methanol) and V (acetic acid)=9:1 as a solvent, the template was removed by Soxhlet extraction. The obtained material was washed with methanol to neutral, and dried in vacuum at 323 K for 6 h to prepare the nicotinamide dummy template surface molecularly imprinted polymer (DMIP).

Comparative Example 1

On the basis of Example 1, addition of the template molecule nicotinamide was omitted, while other parameters remained the same as in Example 1, to obtain a non-imprinted polymer DNIP.

FIG. 2A, FIG. 2B, FIG. 2C, FIG. 2D shows the SEM images of DMIP and DNIP. Comparing FIG. 2A and FIG. 2B with FIG. 2C and FIG. 2D, it can be clearly seen that DMIP presents a network-like branch structure, which is looser and more porous than DNIP, and has obvious agglomeration. This is because nicotinamide is added as a dummy template molecule to DMIP in the preparation process. After the template molecule is eluted, space structures complementary to the corresponding structure are left. These space structures make DMIP look rougher and fluffier. The surface of DNIP is embedded with silica gel particles, which also shows that the polymerization process of the material is carried out on the surface of the silica gel.

Figure 3:
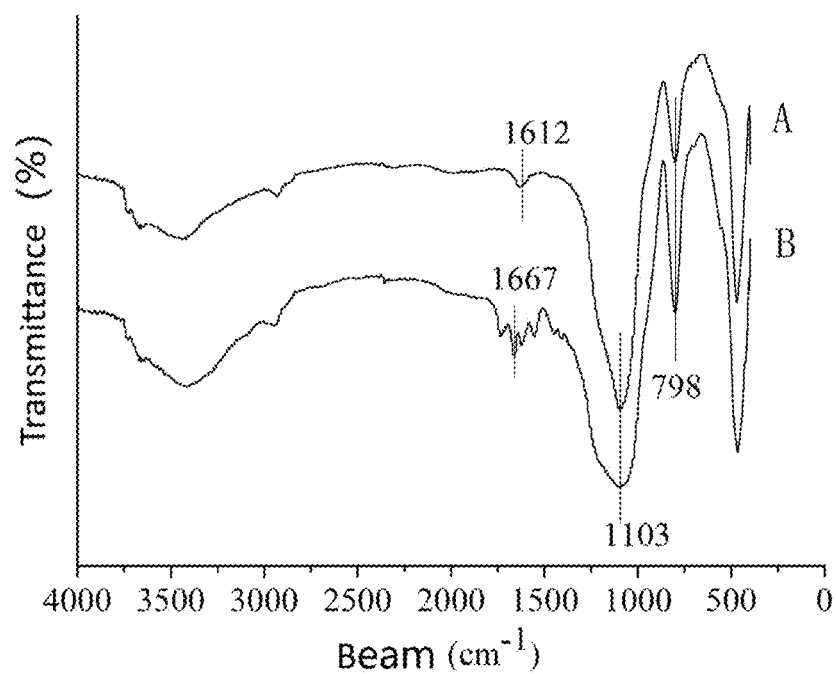
FIG. 3 is an infrared spectrogram of the amino-modified silica gel (A) and the acyl-modified silica gel (B) of Example 1.

FIG. 3 is an infrared spectrogram of the amino-modified silica gel (A) and the acyl-modified silica gel (B) of Example 1. It can be seen from the figure that A is the amino modified silica gel and B is the acyl modified silica gel. The characteristic absorption peaks at 1103 $cm^{-1}$ and 798 $cm^{-1}$ are caused by Si—O—Si stretching vibration in the amino-modified silica gel. The characteristic absorption peak at 1612 $cm^{-1}$ is caused by N—H bending vibration in amino silica gel. This means that the amino-modified silica gel obtained in the experiment was successfully modified by the amino group. Similarly, the characteristic absorption peak, the amide peak at 1667 $cm^{-1}$, of Si—O—Si stretching vibration in the acyl-modified silica gel can also be found in the figure. This indicates that the acyl-modified silica gel was also successfully prepared.

Figure 4:
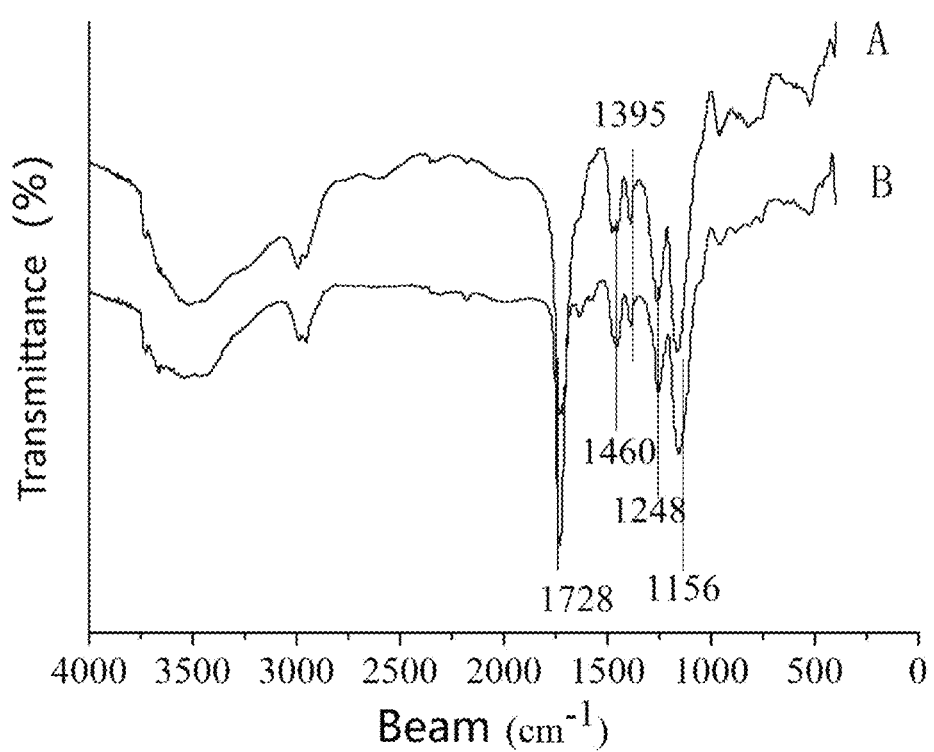
FIG. 4 is an infrared spectrogram of DMIP (A) of Example 1 and DNIP (B) of Comparative Example 1.

FIG. 4 is an infrared spectrogram of DMIP (A) of Example 1 and DNIP (B) of Comparative Example 1. It can be seen from the figure that A is DMIP, B is DNIP and DMIP have similar structures with DNIP because they have highly consistent characteristic peaks. The peak at 1732 $cm^{-1}$ is caused by stretching vibration of C=O in MAA and EGDMA. In addition, the peaks at 1462 $cm^{-1}$, 1393 $cm^{-1}$, and 1157 $cm^{-1}$ are caused by C—H bending vibrations at —$CH_3$ and —$CH_2$. The bending vibration of C—O triggers the characteristic peaks at 1259 $cm^{-1}$.

Example 2

The volume ratio of methanol to water in Example 1 was adjusted as shown in Table 1, while other parameters remained the same as in Example 1, to obtain a nicotinamide dummy template surface molecularly imprinted polymer (DMIP).

A polar solvent of an aqueous system can effectively increase the recognition performance of a molecularly imprinted polymer in the water phase. Using $Q_{DMIP}$ and α as indicators, the influence of the ratio of methanol to water in the solvent on the molecular imprinting effect was investigated. The results are as shown in Table 1. The results show that when the ratio of methanol to water in the solvent is 90:10, $Q_{DMIP}$ and α are optimal. This may be because adding an appropriate amount of water can increase the electrostatic and hydrophobic interactions between MAA and the template molecule, thereby enhancing the specific recognition ability of the template molecule in the water phase. However, when the content of water in the solvent is too much, it will seriously interfere with the formation of hydrogen bonds between the template molecule and the functional monomer.

TABLE 1

The influence of solvent ratio on the molecular imprinting effect

| v (methanol)/v (water) | $Q_{DMIP}$ (mg/g) | $Q_{DNIP}$ (mg/g) | α |
|---|---|---|---|
| 100:0 | 27.02 ± 0.35 | 17.55 ± 0.83 | 1.54 ± 0.07 |
| 90:10 | 31.95 ± 0.86 | 21.31 ± 0.69 | 2.18 ± 0.09 |
| 80:20 | 28,36 ± 0.37 | 16.78 ± 0.36 | 1.69 ± 0.16 |
| 70:30 | 19.83 ± 0.44 | 15.49 ± 0.84 | 1.28 ± 0.21 |
| 60:40 | 14.41 ± 0.25 | 12.32 ± 0.26 | 1.17 ± 0.04 |

Example 3

The amount of the acyl-modified silica gel in Example 1 was adjusted as shown in Table 2, while other parameters remained the same as in Example 1, to obtain a nicotinamide dummy template surface molecularly imprinted polymer (DMIP).

The amount of the modified silica gel will have a great influence on the adsorption effect of the molecularly imprinted polymer. If the amount of the modified silica gel is too small, a part of the template molecules and functional monomers will not be polymerized on the surface of the modified silica gel, thus making the imprinting layer thicker and affecting the specific adsorption effect. When the amount of the modified silica gel is too much, not only the silica gel particles are caused to agglomerate, but also the imprinting layer on the surface of the silica gel is caused to be too thin, thus reducing effective imprinting sites per unit mass of polymer. Using $Q_{DMIP}$ and $\alpha$ as indicators, the influence of the amount of acyl silica gel on the molecular imprinting effect was investigated, and the results are shown in Table 2. The experimental results show that the optimal amount of the acyl-modified silica gel is 0.9 g when $Q_{DMIP}$ and $\alpha$ are optimal.

TABLE 2

The influence of the amount of acyl silica gel on the molecular imprinting effect

| Amount of acyl silica gel (g) | $Q_{DMIP}$ (mg/g) | $Q_{DNIP}$ (mg/g) | $\alpha$ |
|---|---|---|---|
| 0.5 | 30.72 ± 0.62 | 28.63 ± 0.72 | 1.15 ± 0.14 |
| 0.7 | 30.00 ± 0.29 | 18.07 ± 0.18 | 1.66 ± 0.08 |
| 0.9 | 32.42 ± 0.43 | 16.05 ± 0.93 | 2.16 ± 0.03 |
| 1.1 | 28.30 ± 0.63 | 22.54 ± 0.95 | 1.25 ± 0.13 |
| 1.3 | 22.42 ± 0.25 | 19.53 ± 0.26 | 1.21 ± 0.04 |

Example 4

The molar ratio of the cross-linking agent EGDMA to the functional monomer MAA in Example 1 was adjusted as shown in Table 3, while other parameters remained the same as in Example 1, to obtain a nicotinamide dummy template surface molecularly imprinted polymer (DMIP).

The molar ratio of the amount of the cross-linking agent to the functional monomer can affect the number of specific adsorption sites of the molecule, thereby affecting the adsorption effect. Using $Q_{DMIP}$ and $\alpha$ as indicators, the influence of the molar ratio of the amount of the cross-linking agent to the functional monomer on the molecular imprinting effect was investigated, and the results are as shown in Table 3. From the experimental results, if $Q_{DMIP}$ and $\alpha$ are to reach optimal conditions, the molar ratio of the amount of the cross-linking agent to the functional monomer is 7:1. This may be because when the amount of the cross-linking agent added is less, the degree of cross-linking of the molecularly imprinted polymer is lower, such that the functional monomer and the template molecule cannot be sufficiently fixed, thus enough space sites are difficult to form in an orderly arrangement. When the amount of the cross-linking agent added is too much, the degree of cross-linking of the molecularly imprinted polymer is higher, and fewer specific recognition holes are produced per unit mass of the polymer, thereby affecting the imprinting effect of the polymer.

TABLE 3

The influence of the molar ratio of the cross-linking agent to the functional monomer on the molecular imprinting effect

| n (EGDMA)/n (MAA) | $Q_{DMIP}$ (mg/g) | $Q_{DNIP}$ (mg/g) | $\alpha$ |
|---|---|---|---|
| 5:1 | 20.89 ± 0.37 | 14.31 ± 0.73 | 1.46 ± 0.07 |
| 6:1 | 23.12 ± 0.82 | 14.82 ± 0.91 | 1.56 ± 0.16 |
| 7:1 | 32.42 ± 0.75 | 16.05 ± 0.48 | 2.16 ± 0.13 |
| 8:1 | 26.50 ± 0.29 | 16.16 ± 0.63 | 1.64 ± 0.09 |
| 9:1 | 24.13 ± 0.86 | 19.78 ± 0.38 | 1.22 ± 0.10 |

Example 5 Removal of Imidacloprid and Acetamiprid from Tea Polyphenol Aqueous Solution The application of the nicotinamide dummy template surface molecularly imprinted polymer prepared in Example 1 in the removal of imidacloprid and acetamiprid from a tea polyphenol aqueous solution includes 4 steps: preparation of a dummy template molecular imprinted solid phase extraction column, preparation and pretreatment of a tea polyphenol aqueous solution, column adsorption and recycling of an adsorption column. The specific operation method is as follows:

1) Preparation of a Molecularly Imprinted Column:

After 1000 mg of nicotinamide dummy template surface molecularly imprinted polymer (DMIP) powder was mixed with 5 mL of ultrapure water, the mixture was wetly packed into an SPE small column with a lower sieve plate, and pressed into an upper sieve plate to obtain a molecularly imprinted solid phase extraction column.

2) Preparation and Pretreatment of a Tea Polyphenol Aqueous Solution:

After 2.0 g of tea polyphenol solid was weighed and added to 100 mL of ultrapure aqueous solution to prepare a 20 g/L tea polyphenol solution, imidacloprid and acetamiprid were added to make the concentrations 10 μg/mL respectively, the solution was filtered through a 0.25 μm membrane for later use.

3) Column Adsorption:

10 mL of the tea polyphenol aqueous solution in the step 2) flowed through the DMIP solid phase extraction column prepared in the 1), and the flow rate was adjusted to 1.5 mL/min. After the tea polyphenol solution completely flowed through, weakly retained compounds were eluted with 20 mL of ultrapure water. The adsorption solutions were mixed and the concentrations of imidacloprid, acetamiprid and tea polyphenols were measured before and after adsorption.

The test results showed that the adsorption rate of the adsorption column for imidacloprid was 98.6%, the adsorption rate for acetamiprid was 95.3%, and the adsorption rate for tea polyphenols was only 7.2%.

4) Elution:

The imidacloprid and acetamiprid on the adsorption column in the 3) were eluted off with 40 mL of methanol-acetic acid (v/v, 9:1) mixed solvent, the flow rate was adjusted and controlled to 1.5 mL/min, and the eluents were mixed for detection.

The test results showed that 97.8% of imidacloprid and 98.2% of acetamiprid on the adsorption column were eluted off by the eluent.

5) Recycling of an Adsorption Column

After the tea polyphenol aqueous solution in the 2) was cyclically adsorbed 10 times, the adsorption rates for imidacloprid and acetamiprid still reached 88.9% and 87.6%.

Example 6 Removal of Imidacloprid and Acetamiprid from a Large Volume of Tea Polyphenol Aqueous Solution Based on the method in Example 5, the treatment amount of the tea polyphenol aqueous solution was increased, and the specific operation method is as follows:
1) Preparation of a Molecularly Imprinted Column:

After 1000 mg of DMIP powder was mixed with 5 mL of ultrapure water, the mixture was wetly packed into an SPE small column packed with a lower sieve plate, and pressed into an upper sieve plate to obtain a molecularly imprinted solid phase extraction column.
2) Preparation and Pretreatment of a Tea Polyphenol Aqueous Solution:

After 2.0 g of tea polyphenol solid was weighed and added to 100 mL of ultrapure aqueous solution to prepare a 20 g/L tea polyphenol solution, imidacloprid and acetamiprid were added to make the concentrations 10 µg/mL respectively, and the solution was filtered through a 0.25 µm membrane for later use.
3) Column Adsorption:

50 mL of the tea polyphenol aqueous solution in the step 2) flowed through the DMIP solid phase extraction column prepared in the 1), and the flow rate was adjusted to 1.5 mL/min. After the tea polyphenol solution completely flowed through, weakly retained compounds were eluted with 20 mL of ultrapure water, and the adsorption solutions were mixed and the concentrations of imidacloprid, acetamiprid and tea polyphenols were measured before and after adsorption.

The test results showed that the adsorption rate of the adsorption column for imidacloprid was 97.2%, the adsorption rate for acetamiprid was 94.8%, and the adsorption rate for tea polyphenols was only 5.8%.
4) Elution:

The imidacloprid and acetamiprid on the adsorption column in the 3) were eluted off with 80 mL of methanol-acetic acid (v/v, 9:1) mixed solvent, the flow rate was adjusted and controlled to 1.5 mL/min, and the eluents were mixed for detection.

The test results showed that 96.5% of imidacloprid and 96.9% of acetamiprid on the adsorption column were eluted by the eluent.
5) Recycling of an Adsorption Column After the tea polyphenol aqueous solution in the 2) was cyclically adsorbed 10 times, the adsorption rates for imidacloprid and acetamiprid still reached 87.6% and 85.2%.

Example 7 Removal of Imidacloprid and Acetamiprid from Theanine Aqueous Solution Based on the method in Example 5, the tea polyphenol aqueous solution was changed to theanine aqueous solution, and the specific operation method is as follows:
1) Preparation of a Molecularly Imprinted Column:

After 1000 mg of DMIP powder was mixed with 5 mL of ultrapure water, the mixture was wetly packed into an SPE small column packed with a lower sieve plate, and pressed into an upper sieve plate to obtain a molecularly imprinted solid phase extraction column.

2) Preparation and Pretreatment of Theanine Aqueous Solution:

After 2.0 g of theanine was weighed and added to 100 mL of ultrapure aqueous solution to prepare a 20 g/L theanine solution, imidacloprid and acetamiprid were added to make the concentrations 10 µg/mL respectively, and the solution was filtered through a 0.25 µm membrane for later use.
3) Column Adsorption:

10 mL of the theanine aqueous solution in the step 2) flowed through the DMIP solid phase extraction column prepared in the 1), and the flow rate was adjusted to 1.5 mL/min. After the tea polyphenol solution completely flowed through, weakly retained compounds were eluted with 20 mL of ultrapure water, and the adsorption solutions were mixed and the concentrations of imidacloprid, acetamiprid and theanine were measured before and after adsorption.

The test results showed that the adsorption rate of the adsorption column for imidacloprid was 98.5%, the adsorption rate for acetamiprid was 96.3%, and the adsorption rate for theanine was only 6.4%.
4) Elution:

The imidacloprid and acetamiprid on the adsorption column in the 3) were eluted off with 40 mL of methanol-acetic acid (v/v, 9:1) mixed solvent, the flow rate was adjusted and controlled to 1.5 mL/min, and the eluents were mixed for detection.

The test results showed that 97.2% of imidacloprid and 97.6% of acetamiprid on the adsorption column were eluted by the eluent.
5) Recycling of an Adsorption Column After the theanine aqueous solution in the 2) was cyclically adsorbed 10 times, the adsorption rates for imidacloprid and acetamiprid still reached 89.2% and 87.4%.

What is claimed is:

1. A method of using a nicotinamide dummy template surface molecularly imprinted polymer (DMIP), comprising preparing the DMIP, and adding the DMIP in a tea extract aqueous solution and removing imidacloprid and acetamiprid from the tea extract aqueous solution, wherein a preparation method of the nicotinamide dummy template surface molecularly imprinted polymer comprises the following steps:

A1. preparation of a modified silica gel carrier soaking granular silica gel in hydrochloric acid for treatment, filtering and washing the silica gel to neutral and drying the silica gel; in g/mL, mixing the dried silica gel with toluene in a mass-volume ratio of 1:40-1:8; adding 3-aminopropyltriethoxysilane (APTS) and pyridine dropwise, and at a reaction temperature of 363-383 K in a nitrogen atmosphere, performing refluxing for 20-30 h; after washing the obtained mixture with toluene, acetone, ether and methanol, performing vacuum drying to prepare amino-modified silica gel;

in g/mL, mixing the amino-modified silica gel with toluene in a mass-volume ratio of 1:40-1:8; adding acryloyl chloride in a nitrogen atmosphere, adding triethylamine dropwise after magnetic stirring, and performing stirring at room temperature for reacting for 20-30 h; and after washing the obtained mixture with toluene, acetone, ether and methanol, performing vacuum drying to prepare acyl-modified silica gel; and A2. preparation of a dummy template surface molecularly imprinted polymer in g/mL, dissolving nicotinamide in a methanol aqueous solution at a mass-volume ratio of 1:1-3:1; adding the acyl-modified silica gel and methacrylic acid (MAA), and after ultrasonic dispersion, reacting for 2-6 h in the dark, wherein a mass ratio of the nicotinamide to the acyl-modified silica gel is 5:6-5:3; after the reaction, adding ethylene glycol dimethacrylate (EGDMA) and azobisisobutyronitrile (AIBN) in a nitrogen atmosphere, and performing sealed reaction at 323-343 K in a water bath for 20-28 h; and removing a template by Soxhlet extraction, and performing washing and drying to prepare the dummy template surface molecularly imprinted polymer.

2. The method according to claim 1, wherein the step of removing imidacloprid and acetamiprid from tea extract aqueous solution with the nicotinamide dummy template surface molecularly imprinted polymer is as follows:

S1. preparation of a molecularly imprinted solid phase adsorption column wetly packing DMIP into a solid-phase extraction (SPE) small column packed with a lower sieve plate, and pressing into an upper sieve plate to obtain a molecularly imprinted solid phase adsorption column; and adding methanol to activate the column for later use;

S2. removal application adding imidacloprid and acetamiprid to the tea extract aqueous solution with a concentration of 10-60 wt %, so that the imidacloprid and acetamiprid each have a concentration of 1-20 μg/mL; using the aqueous solution as loading solution, and using the molecularly imprinted solid phase adsorption column prepared in S1 for adsorption; controlling a flow rate of the loading solution; washing off weakly retained compounds with 2-8 column volumes of deionized water; mixing an eluent and the column fluid and detecting the mixed solution; and S3. recycling eluting the molecularly imprinted solid phase adsorption column adsorbed with the imidacloprid and acetamiprid in S2 with a mixed solvent of methanol-acetic acid in a volume ratio of 9:1, and adjusting and controlling the flow rate to 0.5-2 mL/min to recycle the adsorption column.

3. The method according to claim 2, wherein a loss rate of water-soluble tea extracts in S2 is less than 10%, while removal rates of imidacloprid and acetamiprid are greater than 96% and 93%, respectively.

4. The method according to claim 2, wherein 96% or more of imidacloprid and 98% or more of acetamiprid in the molecularly imprinted solid phase adsorption column in S3 are eluted.

5. The method according to claim 1, wherein tea extracts are tea polyphenols or theanine.

6. The method according to claim 1, wherein a weight percentage of water-soluble tea extracts is 20-50 wt %.

* * * * *